United States Patent
Banas et al.

(10) Patent No.: US 7,235,092 B2
(45) Date of Patent: Jun. 26, 2007

(54) GUIDEWIRES AND THIN FILM CATHETER-SHEATHS AND METHOD OF MAKING SAME

(75) Inventors: Christopher E. Banas, San Antonio, TX (US); Steven R. Bailey, San Antonio, TX (US); Christopher T. Boyle, San Antonio, TX (US)

(73) Assignee: Advanced Bio Prosthetic Surfaces, Ltd., San Antonio, TX (US)

(*) Notice: Subject to any disclaimer, the term of this patent is extended or adjusted under 35 U.S.C. 154(b) by 742 days.

(21) Appl. No.: 10/136,001

(22) Filed: Apr. 29, 2002

(65) Prior Publication Data

US 2002/0165600 A1 Nov. 7, 2002

Related U.S. Application Data

(63) Continuation-in-part of application No. 09/443,929, filed on Nov. 19, 1999, now Pat. No. 6,379,383.

(60) Provisional application No. 60/318,730, filed on Sep. 12, 2001.

(51) Int. Cl.
*A61F 2/06* (2006.01)
(52) U.S. Cl. .................................... 623/1.11
(58) Field of Classification Search ........ 606/191–198; 623/1.11, 1.12, 1.18, 1.2, 1.34, 1.39, 1.44; 600/434, 585
See application file for complete search history.

(56) References Cited

U.S. PATENT DOCUMENTS 4,510,182 A 4/1985 Cornils et al.
4,516,972 A 5/1985 Samson
4,538,622 A 9/1985 Samson et al.
4,554,929 A 11/1985 Samson et al.
4,616,652 A 10/1986 Simpson
4,665,906 A 5/1987 Jervis
4,748,986 A 6/1988 Morrison et al.
4,751,099 A 6/1988 Niino et al.
4,846,834 A 7/1989 von Recum et al.
4,925,445 A 5/1990 Sakamoto et al.
5,049,251 A 9/1991 Inone (Continued)

FOREIGN PATENT DOCUMENTS

DE 1452370 3/1969

(Continued)

OTHER PUBLICATIONS

F. Goldberg et al., "The Effects of Ion Irradiation on NiTi Shape Memory Alloy Thin Films," *Proceedings of the Second International Conference on Shape Memory and Superelastic Technologies Asilomar Conference Center,* Pacific Grove, California, USA, pp. 177-182 (1997).

(Continued)

*Primary Examiner*—Kevin T. Truong
(74) *Attorney, Agent, or Firm*—David G. Rosenbaum; Paul J. Lee; Rosenbaum & Associates, PC

(57) ABSTRACT

Guidewires and thin-film catheter-sheaths, fabricated using vacuum deposition techniques, which are monolayer or plural-layer members having ultra-thin wall thicknesses to provide very-low profile delivery assemblies for introduction and delivery of endoluminal devices.

13 Claims, 2 Drawing Sheets

U.S. PATENT DOCUMENTS

| | | |
|---|---|---|
| 5,061,914 A | 10/1991 | Busch et al. |
| 5,084,151 A | 1/1992 | Vallana |
| 5,133,845 A | 7/1992 | Vallana et al. |
| 5,135,503 A | 8/1992 | Abrams |
| 5,158,750 A | 10/1992 | Finicie |
| 5,242,710 A | 9/1993 | Claar et al. |
| 5,277,933 A | 1/1994 | Claar et al. |
| 5,329,514 A | 7/1994 | Eguchi et al. |
| 5,341,818 A | 8/1994 | Abrams et al. |
| 5,370,684 A | 12/1994 | Vallana et al. |
| 5,376,463 A | 12/1994 | Bak et al. |
| 5,387,247 A | 2/1995 | Vallana et al. |
| 5,411,476 A | 5/1995 | Abrams et al. |
| 5,421,955 A | 6/1995 | Lau et al. |
| 5,477,864 A | 12/1995 | Davidson |
| 5,514,154 A | 5/1996 | Lau et al. |
| 5,540,820 A | 7/1996 | Terakado et al. |
| 5,545,210 A | 8/1996 | Hess et al. |
| 5,569,295 A | 10/1996 | Lam |
| 5,593,442 A | 1/1997 | Klein |
| 5,603,721 A | 2/1997 | Lau et al. |
| 5,605,714 A | 2/1997 | Dearnaley et al. |
| 5,607,445 A | 3/1997 | Summers |
| 5,607,463 A | 3/1997 | Schwartz et al. |
| 5,609,629 A | 3/1997 | Fearnot et al. |
| 5,628,788 A | 5/1997 | Pinchuk |
| 5,630,840 A | 5/1997 | Mayer |
| 5,647,858 A | 7/1997 | Davidson |
| 5,649,951 A | 7/1997 | Davidson |
| 5,656,036 A | 8/1997 | Palmaz |
| 5,683,453 A | 11/1997 | Palmaz |
| 5,685,961 A | 11/1997 | Pourrezaei et al. |
| 5,690,644 A * | 11/1997 | Yurek et al. ............... 606/198 |
| 5,690,670 A | 11/1997 | Davidson |
| 5,723,219 A | 3/1998 | Kolluri |
| 5,725,573 A | 3/1998 | Dearnaley et al. |
| 5,728,158 A | 3/1998 | Lau et al. |
| 5,735,896 A | 4/1998 | Amon et al. |
| 5,744,515 A | 4/1998 | Clapper |
| 5,765,418 A | 6/1998 | Rosenberg |
| 5,772,864 A | 6/1998 | Moller et al. |
| 5,776,161 A | 7/1998 | Globerman |
| 5,780,807 A | 7/1998 | Saunders |
| 5,782,908 A | 7/1998 | Cahalan et al. |
| 5,782,910 A | 7/1998 | Davidson |
| 5,788,558 A | 8/1998 | Klein |
| 5,798,042 A | 8/1998 | Chu et al. |
| 5,811,151 A | 9/1998 | Hendricks et al. |
| 5,824,045 A | 10/1998 | Alt |
| 5,824,049 A | 10/1998 | Ragheb |
| 5,824,056 A | 10/1998 | Rosenberg |
| 5,840,009 A | 11/1998 | Fischell et al. |
| 5,843,117 A | 12/1998 | Alt et al. |
| 5,843,289 A | 12/1998 | Lee et al. |
| 5,849,206 A | 12/1998 | Amon et al. |
| 5,855,600 A | 1/1999 | Alt |
| 5,855,802 A | 1/1999 | Acciai et al. |
| 5,855,955 A | 1/1999 | Claar et al. |
| 5,858,556 A | 1/1999 | Eckert et al. |
| 5,866,113 A | 2/1999 | Hendricks et al. |
| 5,868,782 A | 2/1999 | Frantzen |
| 5,873,904 A | 2/1999 | Ragheb et al. |
| 5,876,432 A | 3/1999 | Lau et al. |
| 5,879,370 A | 3/1999 | Fischell et al. |
| 5,891,507 A | 4/1999 | Jayaraman |
| 5,895,406 A | 4/1999 | Gray et al. |
| 5,899,935 A | 5/1999 | Ding |
| 5,907,893 A | 6/1999 | Zadno-Azizi |
| 5,913,896 A | 6/1999 | Boyle et al. |
| 5,919,225 A | 7/1999 | Lau et al. |
| 5,925,063 A | 7/1999 | Khosravi |
| 5,932,299 A | 8/1999 | Katoot |
| 5,938,682 A | 8/1999 | Hojeibane et al. |
| 5,938,697 A | 8/1999 | Killion et al. |
| 5,945,153 A | 8/1999 | Dearnaley |
| 5,951,881 A | 9/1999 | Rogers et al. |
| 5,955,588 A | 9/1999 | Tsang et al. |
| 5,962,138 A | 10/1999 | Kolluri et al. |
| 5,968,091 A | 10/1999 | Pinchuk et al. |
| 5,972,018 A | 10/1999 | Israel et al. |
| 5,972,027 A | 10/1999 | Johnson |
| 5,984,905 A | 11/1999 | Dearnaley et al. |
| 6,013,855 A | 1/2000 | McPherson et al. |
| 6,015,429 A | 1/2000 | Lau et al. |
| 6,019,784 A | 2/2000 | Hines |
| 6,022,370 A | 2/2000 | Tower |
| 6,027,526 A | 2/2000 | Limon et al. |
| 6,033,433 A | 3/2000 | Ehr et al. |
| 6,042,597 A | 3/2000 | Kveen et al. |
| 6,056,776 A | 5/2000 | Lau et al. |
| 6,059,808 A | 5/2000 | Boussignac |
| 6,066,167 A | 5/2000 | Lau et al. |
| 6,066,168 A | 5/2000 | Lau et al. |
| 6,066,169 A | 5/2000 | McGuiness |
| 6,071,305 A | 6/2000 | Brown et al. |
| 6,086,773 A | 7/2000 | Dufresne et al. |
| 6,096,175 A | 8/2000 | Roth |
| 6,106,642 A | 8/2000 | DiCarlo et al. |
| 6,203,505 B1 | 3/2001 | Jalisi et al. |
| 6,241,690 B1 | 6/2001 | Burkett et al. |
| 6,280,539 B1 | 8/2001 | Abrams et al. |
| 6,312,463 B1 | 11/2001 | Rourke et al. |
| 6,491,619 B1 * | 12/2002 | Trauthen et al. ............... 600/3 |
| 6,669,721 B1 * | 12/2003 | Bose et al. ............... 623/1.15 |
| 2001/0003146 A1 | 6/2001 | Jalisi et al. |
| 2001/0039449 A1 | 11/2001 | Johnson et al. |

FOREIGN PATENT DOCUMENTS

| | | |
|---|---|---|
| EP | 0400947 | 12/1990 |
| EP | 0442303 | 8/1991 |
| JP | 51055724 | 5/1976 |
| JP | 60162761 | 8/1985 |
| JP | 61-88135 | 7/1994 |
| JP | 11267462 | 10/1999 |
| WO | WO 97/07257 | 2/1997 |
| WO | WO 97/44692 | 11/1997 |
| WO | WO 98/13537 | 4/1998 |
| WO | WO 98/45506 | 10/1998 |
| WO | WO 99/23977 | 5/1999 |
| WO | WO 01/53559 | 7/2001 |
| WO | WO 01/55473 | 8/2001 |
| WO | WO 01/56502 | 8/2001 |

OTHER PUBLICATIONS

L. Buchaillot et al., "Constitutive Parts of a Shape Memory Alloy Titanium Nickel Thin Film Catheter," *Proceedings of the Second International Conference on Shape Memory and Superelastic Technologies Asilomar Conference Center*, Pacific Grove, California, USA, pp. 183-188 (1997).

Q. Pingshan et al., "The Effect of HCD Technological Factors on the NiTi SMA Film Thickness," *Proceedings of the Second International Conference on Shape Memory and Superelastic Technologies Asilomar Conference Center*, Pacific Grove, California, USA, pp. 173-176 (1997).

H. Weixin et al., "The Characteristics of NiTi HCD-Deposited SMA Films," *Proceedings of the Second International Conference on Shape Memory and Superelastic Technologies Asilomar Conference Center*, Pacific Grove, California, USA, pp. 167-172 (1997).

A. Ishida et al., "Microstructure of Ti-Rich TiNi Thin Films," *Proceedings of the Second International Conference on Shape Memory and Superelastic Technologies Asilomar Conference Center*, Pacific Grove, California, USA, pp. 161-166 (1997).

"Thin Film Shape Memory Alloy Microactuators," by TiNi Alloy Company (online).

Johnson et al., "Progress in Thin Film Shape Memory Microactuators," www.sma-mems.com/recent.htm (Overview), pp. 1-5.

W. Ensinger, "The influence of ion irradiation during film growth on the chemical stability of film/substrate systems," *Surface and Coatings* Technology, 80:35-48 (1996).

"Sputtering Targets High-Quality Thin Film Materials," by AMETEK Specialty Metal Products online at www.ametek84.com/fd-sputtering.html, pp. 1-3.

D. Mattox, "A Concise History of Vacuum Coating Technology, Part 2: 1940 to 1975," www.svc.org/HistoryofVac2.html, pp. 1-15.

M. Mrksich, "Model Surfaces for Studying and Controlling the Adhesion of Cells," AVS 47th International Symposium, Invited Paper No. BI+EL-TuA1 (Oct. 3, 2000).

D.S. Sutherland et al., "Cell Response to Chemically and Topographically Modified Surfaces," AVS 47th International Symposium, Paper No. BI+EL-TuA3 (Oct. 3, 2000).

T. Nishikawa et al., "Tissue Formation of Hepatocyles on Micro-Porous Films of Polylactide," AVS 47th International Symposium, Paper No. BI+EL-TuA10 (Oct. 3, 2000).

R. Daw et al., "Endothelial Cell Organization on Micropatterned Protein Surfaces," AVS 47th International Symposium, Paper No. BI-WeP21 (Oct. 4, 2000).

J.E. Houston, "The Nanomechanical Properties of Thin Films," AVS 47th International Symposium, Paper No. TF-TuA1 (Oct. 3, 2000).

E. Kusano et al., "Anomalous Plastic and Elastic Behaviours of Sputter-deposited TiN with 10 or 20 Inserted Thin Al Layers Evaluated by Nanoindentation," AVS 47th International Symposium, Paper No. TF-TuA3 (Oct. 3, 2000).

A.D. Johnson et al., "Recent Progress in the Application of Thin Film Shape Memory Alloys," *Proceedings of the First International Conference on Shape Memory and Superelastic Technologies Asilomar Conference Center*, Pacific Grove, California, USA, pp. 299-310 (1994).

J.D. Busch et al., "Shape Memory Properties in NiTi Sputter-deposited Film," *J Appl. Phys.*, 68(12):6224-6226 (Dec. 15, 1990).

J.A. Waker et al., "Thin-film Processing of TiNi Shape Memory Alloy," *Sensors and Actuators*, A21-A23, pp. 243-246 (1990).

E. Quandt et al., "Sputter-deposition of TiNi, TiNiPd and TiPd films displaying the two-way shape-memory effect," *Sensors and Actuators*, A 53, pp. 434-439 (1996).

V.V. Martynov, "Applications of Shape-Memory Alloy Thin Films," *Proceedings of the Second International Conference on Shape Memory and Superelastic Technologies Asilomar Conference Center*, Pacific Grove, California, USA, pp. 1-8 (1997); and.

"Multicomponent Film Deposition by Target Biasing," *IBM Technical Disclosure Bulletin*, pp. 1-2 (Jul. 1980).

M. Kohl et al., "Thin film shape memory microvalves with adjustable operation temperature," *Sensors and Actuators*, 83(1-3):214-219 (May 2000).

Gordon et al., "Liquid Sources for Chemical Vapor Deposition of Group 6 Metals and Metal Nitrides," www.techtransfer.harvard.edu/cgi-bin/TALSearch.cgi?full_report=1&case=3, Case No. 1709.

Curtis et al., "Reactions of Biological Cells to Nanostructures," AVS 46th International Symposium, Paper BI-WeM2 (Oct. 27, 1999).

"Fabrication of Small-Scale Coils and Bands as Photomasks on Optical Fibers for Generation of In-Fiber Gratings, Electromagnets as Micro-NMR Coils, Microtransformers, and Intra-Vascular Stents," www.techtransfer.harvard.edu/cgi-bin/TALSearch.cgi?full_report=1&case=72, Case No. 1263.

"Biocompatibility of Cardiac Cells on Silane-Modified Surfaces," AVS 46th International Symposium, Paper BI-WeM5 (Oct. 27, 1999).

"Biofunctionalization of Surfaces with Peptide Amphilphiles," AVS 46th International Symposium, Paper No. BI-WeM7 (Oct. 27, 1999).

"Plasma Copolymer Surfaces for Cell Culture," AVS 46th International Symposium, Paper No. BI-WeM9 (Oct. 27, 1999).

"Plasma Co-polymer Surfaces for the Controlled Adsorption of Common Proteins," AVS 46th International Symposium, Paper No. Bl-FrM2 (Oct. 29, 1999).

"Biofilm—Titanium Chemistry of Adhesion Using X-ray Photoelectron Spectroscopy," AVS 46th International Symposium, Paper No. Bl-FrM10 (Date Missing).

"Nanoscale Patterning of Gold for Attachment of Supported Lipid Bilayers," AVS 46th International Symposium, Paper No. Bl-FrM10 (Date Missing).

"Focused Ion Beam NonaFabrication," http://www.glue.umd.edu/~astan/avs04.htm.

"Amorphous Carbon and C:N Thin Films," http:www.glue.umd.edu/~astan/avs01.htm.

"Multilayer Ceramic/Metallic Coatings by Ion Beam-Assisted, Electron Beam Physical Vapor (EB-PVD) Deposition," Penn State Applied Research Laboratory, pp. 1-4 (1997).

"Benefits From Diamond-Like Coated Stainless Steel Stents," http://www.phytis.com/stents0.htm, pp. 1-2.

"Adhesion of Bovine Serus Albumin on Coated DLC (Diamond-Like) and Uncoated ($SiO_2/TiO_2$) Sensor Chips," http://www.phytis.com/stent4.htm, pp. 1-2.

"Flow Cytometric Investigation," http://www.phytis.com/stent6.htm, pp. 1-3.

"Pre-clinical and Clinical Evaluation," http://www.phytis.com/stent2.htm, pp. 1-2.

"The New Phytis Stent," http://www.phytis.com/stent1.htm, pp. 1-2.

"Invulnerability and Resistance of DLC-Coating," http://www.phytis.com/stent3.htm, pp. 1-3.

"Material in Use and Its Biocompatibility," http://www.phytis.com/stent5.htm, pp. 1-2.

"Expertise Concerning the Implementation of the Phytis Diamond as Stent Performed at the Institute for Experimental Medicine (IEM)," http://www.phytis.com/stent9.htm, p. 1.

"PHYTIS L.D.A. Home Page Information," http://www.phytis.com/content/htm, pp. 1-15.

"Risk Analysis of Stents With a Diamond-Like Coated Surface For Use in Prosthetic Implants," http://www.phytis.com/risk.htm, pp. 1-6.

"Directions for Use, DIAMOND AS® Stent," http://www.phytis.com/direcuse.htm, pp. 1-8.

"Stents: Literature," http://www.phytis.com/liter.htm, pp. 1-8.

"Vacuum Conditions for Sputtering Thin Film TiNi," *Journal of Vacuum Science and Technology, JVST A Online*, pp. 1-2 (Abstract view).

Gisser et al., "Oriented nickel-tetanium shape memory alloy films prepared by annealing during deposition," *Applied Physics Letters*, 61(14):1632-1634 (Abstract view) (Date Missing).

K.S. Fancey et al., "Relative importance of bombardment energy and intensity in ion plating," *Journal of Vacuum Science & Technology A: Vacuum, Surfaces and Films*, 13(2):428-435 (Abstract view) (Mar. 1995).

\* cited by examiner

GUIDEWIRES AND THIN FILM CATHETER-SHEATHS AND METHOD OF MAKING SAME

CROSS-REFERENCE TO RELATED APPLICATIONS

This application is a Continuation-In-Part of U.S. patent application Ser. No. 09/443,929 which was filed on Nov. 19, 1999 now U.S. Pat. No. 6,379,383, the disclosure of which is hereby incorporated by reference. This application also claims the benefit of U.S. Provisional Patent Application No. 60/318,730 which was filed on Sep. 12, 2001.

BACKGROUND OF THE INVENTION

The present invention relates generally to the field of medical devices, and more particularly to guiding means such as a guidewire for advancing a catheter within a body lumen to perform a minimally invasive procedure such as percutaneous transluminal coronary angioplasty (PTCA). The present invention further pertains to catheters and sheaths for delivering and deploying an implantable device within a body lumen.

In a typical PTCA procedure a guiding catheter having a preformed distal tip is percutaneously introduced into the cardiovascular system of a patient by means of a conventional Seldinger technique and advanced proximally until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated one or more times to a predetermined size with radiopaque fluid to compress the arteriosclerotic plaque of the lesion against the inside of the artery wall and to otherwise expand the inner lumen of the artery. The balloon is then deflated so that blood flow resumes through the dilated artery and the dilatation catheter is removed.

In a conventional stent delivery procedure, a stent is delivered endoluminally on a delivery catheter, then expanded either by an angioplasty balloon or by removing a constraining sheath and permitting the stent to radially expand by its shape memory, superelastic or self-expanding properties. Conventional guidewires for angioplasty and stent-delivery procedures usually comprise an elongated core member with the distal portion of the core member having one or more tapered sections and a flexible body such as a helical coil disposed about the distal portion of the core member. A shapeable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

Further details of guidewires can be found in U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,748,986 (Morrison et al.); U.S. Pat. No. 5,135,503 (Abrams); U.S. Pat. No. 5,341,818 (Abrams et al.); and U.S. Pat. No. 5,411,476 (Abrams et al.) each of which is hereby incorporated herein in their entirety by reference thereto.

A major requirement for guidewires and other intraluminal guiding members, whether they be solid wire or tubular members, is that they have sufficient column strength to be pushed through a patient's vascular system or other body lumen without kinking. However, they must also be flexible enough to pass through tortuous passageways without damaging the blood vessel or other body lumen through which they are advanced. Efforts have been made to improve both the strength and flexibility of guidewires in order to make them more suitable for their intended uses, but these two properties tend to be diametrically opposed to one another in that an increase in one usually involves a decrease in the other.

The prior art makes reference to the use of alloys such as NITINOL (nickel-titanium alloy) which have shape memory and/or superelastic or pseudoelastic characteristics in medical devices which are designed to be inserted into a patient's body. The shape memory characteristics allow the prior art devices to be deformed while in the martensite phase to facilitate their insertion into a body lumen or cavity and then be heated within the body to transform the metal to the austenite phase so that the device returns to its remembered shape or to exert a force on whatever prevents the device from returning to its zero strain configuration. Superelastic characteristics on the other hand generally allow the metal to be deformed and restrained in the deformed condition to facilitate the insertion of the medical device containing the metal into a patient's body, with such deformation causing the phase transformation, e.g. austenite to martensite. Once within the body lumen the restraint on the superelastic member can be removed, thereby reducing the stress therein so that the superelastic member can return to its original undeformed shape by the transformation back to the original austenite phase or so that the superelastic member can exert a force on whatever prevents the superelastic member from returning to its zero strain configuration. In other applications, the stress induced austenite to martensite transformation is utilized to minimize trauma while advancing a medical device such as a guidewire within a patient's body lumen.

Shape memory or superelastic alloys generally have at least two phases, a martensite phase, which has a relatively low strength and which is stable at relatively low temperatures and higher strains, and an austenite phase, which has a relatively high strength and which is stable at temperatures higher and strains lower than the martensite phase. Shape memory characteristics are imparted to the alloy by heating the metal at a temperature above body temperature, preferably between about 40° to about 60° C., while the metal is kept in a constrained shape and then cooled to ambient temperature. The cooling of the alloy to ambient temperature causes at least part of the austenite phase to transform to the martensite phase which is more stable at this temperature. The constrained shape of the metal during this heat treatment is the shape programmed when the alloy is reheated to these temperatures causing the transformation of the martensite phase to the austenite phase. The metal in the martensite phase may be plastically deformed to facilitate the entry thereof into a patient's body. The metal will remain in the pre-programmed shape even when cooled to a temperature below the transformation temperature back to the martensite phase, so it must be reformed into a more usable shape, if necessary. Subsequent heating of the deformed martensite phase to a temperature above the martensite to austenite transformation temperature causes the deformed martensite phase to transform to the austenite phase and during this phase transformation the metal reverts back to its remembered shape or to exert a force on whatever prevents the device from returning to its zero strain configuration.

When stress is applied to a specimen of a metal such as NITINOL® exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress is necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e., there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The prior art makes reference to the use of metal alloys having superelastic characteristics in medical devices which are intended to be inserted or otherwise used within a patient's body. See for example, U.S. Pat. No. 4,665,906 (Jervis) and U.S. Pat. No. 4,925,445 (Sakamoto et al). The Sakamoto et al. patent discloses the use of a nickel-titanium superelastic alloy in an intravascular guidewire which could be processed to develop relatively high yield strength levels. However, at the relatively high yield stress levels which cause the austenite-to-martensite phase transformation characteristic of the material, it did not have a very extensive stress-induced strain range in which the austenite transforms to martensite at relative constant stress. As a result, frequently as the guidewire was being advanced through a patient's tortuous vascular system, it would be stressed beyond the superelastic region, i.e. develop a permanent set or even kink which can result in tissue damage. This permanent deformation would generally require the removal of the guidewire and the replacement thereof with another. Products of the Jervis patent on the other hand had extensive strain ranges, i.e. 2 to 8% strain, but the relatively constant stress level at which the austenite transformed to martensite was very low, e.g. 50 ksi.

The prior methods of using the shape memory characteristics of these alloys in medical devices intended to be placed within a patient's body presented operational difficulties. For example, with shape memory alloys having a stable martensite temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices could be introduced into a patient's body with little or no problem, but they had to be heated to the martensite-to-austenite transformation temperature which was frequently high enough to cause tissue damage and very high levels of pain.

What has been needed and heretofore unavailable is tubular body for intravascular devices, such as guidewires or catheter-sheaths, which have at least a portion thereof exhibiting superelastic and/or shape memory characteristics and which is fabricated by vacuum deposition techniques to provide precise control over the crystalline structure of the material used to fabricate the device.

BRIEF SUMMARY OF THE INVENTION

The present invention relates to a method of manufacturing a guidewire or a catheter-sheath, each having a body. The body of the inventive guidewire can be generally tubular and define a central lumen or, alternatively, can be solid. The body of the inventive catheter-sheath is generally tubular and defines a central lumen. The method of manufacturing the inventive guidewire or catheter-sheath comprises providing a substrate having a surface capable of accommodating metal deposition thereon and having a substrate geometry corresponding at least in part to a geometry desired for the body, depositing a thin-film of a biocompatible metal onto the substrate using a vacuum deposition technique, the thin-film forming the body, and removing the substrate from the body. The method optionally further comprises subjecting the body to post-deposition annealing.

The vacuum deposition technique can be any vacuum deposition technique such as ion beam-assisted evaporative deposition or sputter deposition (e.g., cylindrical magnetron sputter deposition). In a preferred embodiment, ion beam-assisted evaporative deposition is used and is conducted in the presence of an inert gas such as, for example, argon, xenon, nitrogen, and neon.

In one embodiment, a sacrificial layer is deposited onto the substrate prior to the deposition of the biocompatible metal. Alternatively, the substrate itself comprises a sacrificial material. Removal of the substrate is accomplished by any suitable method, such as etching the sacrificial material. In certain embodiments, the substrate geometry is generally cylindrical having a circular transverse cross-section or, alternatively, an elliptical transverse cross-section.

The biocompatible metal can be selected from the group consisting of elemental titanium, vanadium, aluminum, nickel, tantalum, zirconium, chromium, silver, gold, silicon, magnesium, niobium, scandium, platinum, cobalt, palladium, manganese, molybdenum and alloys thereof, nitinol, and stainless steel.

In one embodiment, the deposition process is repeated a plurality of times to form a plurality of successive layers of the deposited metal. In a preferred embodiment, the successive layers are concentric. In another embodiment, a radiopaque metal is used to form at least one of the layers.

The invention also relates to a guidewire having a body comprising a thin-film of a biocompatible metal formed by a vacuum deposition technique. In certain embodiments of the inventive guidewire, the thin-film comprises a plurality of layers. The invention further relates to a catheter-sheath having a generally tubular body, the body comprising a thin-film of a biocompatible metal formed by a vacuum deposition technique. In certain embodiments of the inventive catheter-sheath, the thin-film comprises a plurality of layers.

The invention also relates to an assembly for delivering a medical device via a patient's vascular system. The inventive assembly comprises (a) a medical device, (b) a guidewire having a guidewire body, the guidewire body comprising a first thin-film of a first biocompatible metal formed by a vacuum deposition technique, and (c) a catheter-sheath having generally tubular catheter-sheath body, the catheter-sheath body comprising a second thin-film of a second biocompatible metal formed by a vacuum deposition technique, the catheter-sheath body defining a catheter-sheath lumen. The assembly is formed by positioning the guidewire coaxially within the lumen of the catheter-sheath and concentrically positioning the medical device within the lumen of the catheter-sheath and intermediate between the catheter-sheath body and the guidewire body. The first and second biocompatible metals can be the same metal or different metals. In one embodiment at least one of the first thin-film and the second thin-film comprises a plurality of layers. In an alternative embodiment, the first thin-film and the second thin-film each comprise a plurality of layers. In a preferred embodiment, a radiopaque metal is used to form at least one of the layers. The medical device can be any medical device that can be delivered via a patient's vascular system, for example, a stent, a graft, a stent-graft, a valve, a filter, an occluder, and a patch.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

DETAILED DESCRIPTION OF THE INVENTION

Figure 1:
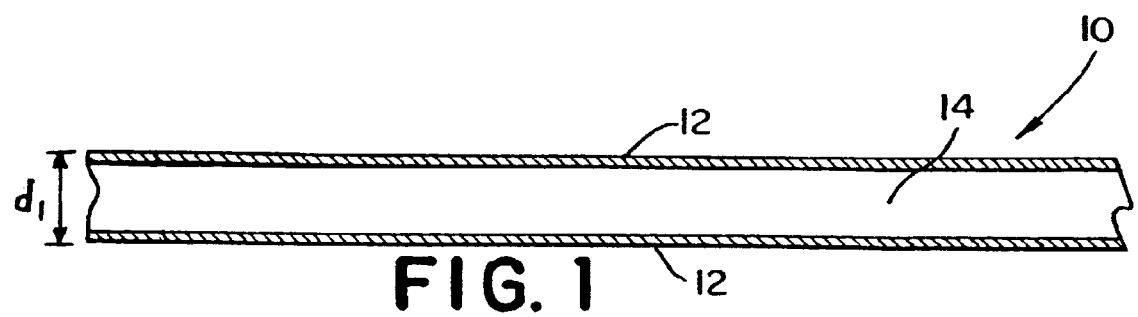
FIG. 1 is a side-elevational cross-sectional view of a guidewire in accordance with the present invention.

The present invention is directed to guidewires and to thin-film catheter-sheaths, wherein each of the guidewire and the thin-film catheter-sheath is fabricated by vacuum deposition techniques, similar to those employed in the microelectronics arts to fabricate semiconductors. Each of the guidewire and the catheter-sheath has a body which is preferably formed either as a single layer tubular member or as a laminated tubular member with plural layers, wherein the layers can be concentrically aligned.

The inventive guidewires and catheter-sheaths provide several advantages over the prior art. Specific examples of such advantages of the inventive metal catheter-sheaths and thin-film guidewires, include: (i) metal catheter-sheaths have the same metallic creep rate as the self-expanding devices that they constrain so they are less likely to deform and take a set during sterilization or during the shelf-life of the product; (ii) by controlling material properties and employing micro-perforations it is possible to impart radial, longitudinal or multi-directional compliance to the catheter-sheath or guidewire such that compliance and or flexibility is constant or varied over the length of the device; (iii) when vacuum deposition is employed in preference to conventional wrought processes and materials, the chemical content, microstructure, mechanical properties, etc., can be precisely controlled throughout the thickness of the film and along the entire length of the device, as opposed to the prior art which requires fusion of multiple sections to impart certain mechanical properties, microstructure, or chemical content; (iv) in addition to providing single layer thin-film devices, the present invention provides for fabricating multilayer devices which exhibit improved strength, biocompatibility, corrosion resistance, fatigue resistance, radiopacity, trackability, pushability and interactions with other medical devices or anatomical structures; and (v) vacuum deposition processes lend themselves to fabricating thinner devices and devices with improved wall thickness uniformity.

The mechanical properties of metals depend significantly on their microstructure. The forming and shaping processes used to fabricate metal foils, wires and thin-walled seamless tubes involves heavy deformation of a bulk material, which results in a heavily strained and deformed grain structure. Even though annealing treatments may partially alleviate the grain deformation, it is typically impossible to revert to well-rounded grain structure and a large range of grain sizes is a common result. The end result of conventional forming and shaping processes, coupled with annealing, typically results in non-uniform grain structure and less favorable mechanical properties in smaller sized wrought metal products. It is possible, therefore, to produce high quality small sized metal products with a homogeneous crystalline structure for a variety of purposes, such as micromechanical devices and medical devices, using vacuum deposition technologies.

In vacuum deposition technologies, materials are formed directly in the desired geometry, e.g., planar, tubular, etc. The common principle of the vacuum deposition processes is to take a material in a minimally processed form (a source material), such as pellets or thick foils, and atomize the material. Atomization may be carried out using heat, as is the case in physical vapor deposition, or using the effect of collisional processes, as in the case of sputter deposition, for example. In some forms of deposition, a process such as laser ablation, which creates microparticles which typically comprise one or more atoms, may replace atomization.

Using laser ablation, the number of atoms per particle may be in the thousands or more. The atoms or microparticles of the source material are then deposited on a substrate or mandrel to directly form the desired object. In other deposition methodologies, chemical reactions between ambient gas introduced into the vacuum chamber, i.e., the gas source, and the deposited atoms and/or particles are part of the deposition process. In this scenario, the deposited material includes compound species that are formed due to the reaction of the solid source and the gas source, such as in the case of chemical vapor deposition. In most cases, the deposited material is then either partially or completely removed from the substrate thereby releasing the desired product.

The rate of film growth is a significant parameter of vacuum deposition processes. In order to deposit materials that can be compared in functionality with wrought metal products, deposition rates in excess of 1 micrometers/hour are a must and indeed rates as high as 100 micrometers per hour are desirable. These are high deposition rates and it is known that at such rates the deposits always have a columnar structure. Depending on other deposition parameters, and most importantly on the substrate temperature, the columns may be amorphous or crystalline, but at such high deposition rates microcrystalline structure development can be expected at best. The difficulty is that the columns provide a mechanically weak structure in which crack propagation can occur uninhibited across the whole thickness of the deposit.

A special advantage of vacuum deposition technologies is that it is possible to deposit layered materials and thus films possessing exceptional qualities may be produced (c.f., H. Holleck, V. Schier: "Multilayer PVD coatings for wear protection", *Surface and Coatings Technology*, Vol. 76–77 (1995) pp. 328–336). Layered materials, such as superstructures or multilayers, are commonly deposited to take advantage of some chemical, electronic, or optical property of the material as a coating; a common example is an antireflective coating on an optical lens.

It has not been recognized until relatively recently that multilayer coatings may have improved mechanical properties compared with similar coatings made of a single layer. The improved mechanical properties may be due to the ability of the interface between the layers to relieve stress. This stress relief occurs if the interface provides a slide plane, is plastic, or may delaminate locally. This property of multilayer films has been recognized in regard with their hardness but this recognition has not been translated to other mechanical properties that are significant for metal products that may be used in application where they replace conventional wrought metal parts.

The process according to the invention can be modified by interrupting film growth at various layers thereby resulting in discontinuous columns that prevent crack propagation across the entire film thickness. In this sense, it is not necessary that the structure comprise a multiplicity of chemically distinct layers, as is common in the case of thin film technology where multilayers are used. Such chemical differences may be useful and may contribute to improved properties of the materials.

In its simplest form, the process of fabricating the inventive multilayer devices comprises the steps of providing a substrate, depositing a first layer of material on the substrate, depositing a second layer of material on the first layer of material and optionally removing the layered material from the substrate. In more complex cases, the number of layers is more than two. There is no limitation regarding the number of layers and regarding the thickness of each layer.

As used in this application a "layer" is intended to mean a substantially uniform material limited by interfaces between it and adjacent other substantially homogeneous layers, substrate, or environment. The interface region between adjacent layers is an inhomogeneous region in which extensive thermodynamic parameters may change. Different layers are not necessarily characterized by different values of the extensive thermodynamic parameters but at the interface, there is a local change at least in some parameters. For example, the interface between two steel layers that are identical in composition and microstructure may be characterized by a high local concentration of grain boundaries due to an interruption of the film growth process. Thus, the interface between layers is not necessarily different in chemical composition if it is different in structure.

It is necessary to provide for good adhesion between the layers and this is usually achieved by providing for a relatively broad interface region rather than for an abrupt interface region. The width of the interface region may be defined as the range within which extensive thermodynamic parameters change. This range can depend on the interface area considered and it may mean the extent of interface microroughness. In other words, adhesion may be promoted by increased interface microroughness between adjacent layers.

By providing for a layered structure, the inventive materials comprise a controlled maximum size of grains and columns as extended defects in the direction of the film growth (perpendicular to the layers). This limit of the grain or defect size results in materials that have increased mechanical strength and particularly increased toughness compared to their non-laminated counterparts, both deposited and wrought materials. In addition, by limiting the extent to which defects and grain boundaries reach across the laminate, corrosion resistance is also improved.

Laminated materials will have additional advantages when chemical compositions of the layers are chosen to achieve special properties. For example, a radiopaque material such as Ta may form one layer of a structure while other layers are chosen to provide the material with necessary mechanical and other properties.

In accordance with a preferred embodiment the present invention, the preferred deposition methodologies include ion-beam assisted evaporative deposition and sputter deposition techniques. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to bulk material properties. Deposition rates up to 20 nanometers per second (nm/sec) are achievable using ion beam-assisted evaporative deposition techniques.

Materials to make the inventive guidewires and thin-film catheter-sheaths are chosen for their biocompatibility, mechanical properties, i.e., tensile strength, yield strength, and their ease of deposition. Examples of such materials include, but are not limited to, elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

The guidewires and thin-film catheter-sheaths of the invention are preferably fabricated of nickel-titanium alloys, and may be doped or laminated with radiopaque materials, such as tantalum (Ta) to enhance the radiopacity of the guidewire under fluoroscopy. In one embodiment, the inventive guidewires and thin-film catheter-sheaths preferably have shape memory or superelastic properties. By way of example, a method of forming the elongated shape memory or superelastic portion of the guidewire or thin-film catheter-sheath can include fabricating a generally tubular member by vacuum depositing nickel-titanium alloy onto a suitable cylindrical substrate, removing the deposited tubular member from the substrate, then heat treating the deposited material at a given temperature between about 450° to about 600° C., preferably about 475° to about 550° C., for between about 0.5 to about 60 minutes to generate superelastic properties. To impart a shape memory, either the entire material or a region or regions of the deposited material can be subjected to shaping stress equal to between about 5% to about 50%, preferably about 10% to about 30%, of the yield stress of the material (as measured at room temperature) during a heat treatment of about 450° to about 600° C. This thermomechanical processing pre-programs a shape memory for the pre-programmed shape to the material and provides relatively uniform residual stress in the material. It is preferable that the alloy composition and thermal treatment are selected to provide an austenite finish transformation temperature generally about −20° C. to about 40° C. and usually less than body temperature (approximately 37° C.). To obtain more consistent final properties, the material may be annealed after deposition. Although an exemplary method of forming the elongated shape memory or superelastic portion of the guidewire or thin-film catheter-sheath has been given, it is to be understood that the present invention is not limited to this particular method, or the given values.

In accordance with a method of the present invention, vacuum deposition methods as are known in the microelectronics and nano-fabrication arts are preferably employed. It is preferable to employ sputtering or ion beam-assisted evaporative deposition to deposit at least one metal film of a biocompatible metal onto a sacrificial substrate. The substrate has a geometry corresponding to the geometry desired for the guidewire and/or thin-film catheter-sheath, e.g., to create tubular body having a circular or elliptical transverse cross-sectional shape, at least one layer of a thin-film of a biocompatible metal is deposited onto the sacrificial substrate. When multiple layers are to be deposited, each layer may have varying properties along the length of the device by varying the local deposition conditions. For example, locally doping the target material with Ti in the case of nitinol deposition to raise the transition temperature, with Ta to increase radiopacity, or with a radioactive isotope to cause local radioactivity. After depositing at least one layer having a desired thickness, the substrate and the deposited thin-film of metal are removed from the deposition chamber and the sacrificial substrate is removed by means suitable for the selected substrate. For example, if a copper substrate is employed, it can be removed by chemical etching. Alternatively, a sacrificial layer of a material, such as carbon or aluminum, may be deposited on the external surface of the substrate prior to depositing the metal. After deposition has occurred, the sacrificial layer can be removed by any suitable process or means, such as, for example, melting, chemical means, ablation, or machining, to free the guidewire or catheter-sheath from the substrate. The entire guidewire or a selected region (or selected regions) of the guidewire may be subject to post-deposition annealing to alter the crystalline structure of the thin-film and effect changes in the material properties of the metal film, such as altering the transition temperature of the annealed regions.

Figure 2:
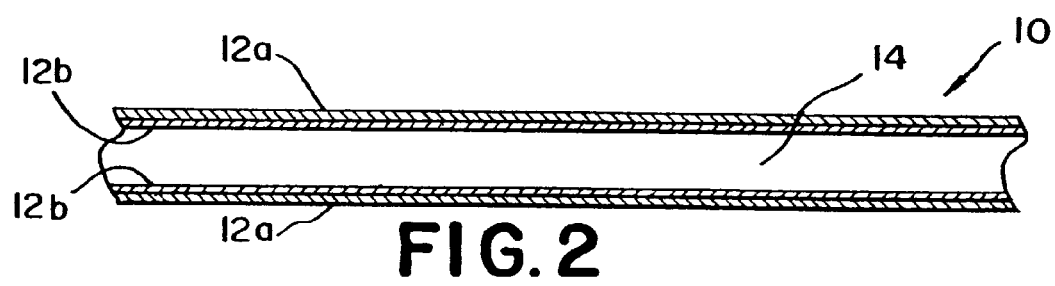
FIG. 2 is a side-elevational cross-sectional view of a second embodiment of a guidewire in accordance with the present invention.

Turning now to the accompanying figures, FIGS. 1 and 2 depict two embodiments of the inventive guidewire 10. In FIG. 1 there is depicted a guidewire body 12 comprising a monolayer of material formed by a vacuum deposition technique, although conventional wrought processes may be employed for certain embodiments such as those where compliance is required. The generally tubular guidewire body 12 has a central guidewire lumen 14 and an outer diameter $d_1$.

FIG. 2 depicts a guidewire 10 having a guidewire body 12 comprising a plurality of layers 12a and 12b formed by a vacuum deposition technique. The guidewire body 12 defines a central guidewire lumen 14. Those skilled in the art will understand that an inventive guidewire 10 having plural layers may be fabricated with at least two layers (12a and 12b) or any number of layers more than two. Additionally, each of the layers may be either continuous or discontinuous about the circumference or length of the tubular guidewire body 12. Variations in continuity or discontinuity of an individual layer can be imparted in order to impart differential material and performance properties to the guidewire 10. A guidewire 10 according to the present invention preferably has an outer diameter $d_1$ between about 0.2 millimeters (mm) to about 0.75 millimeters (mm), with a wall thickness between about 0.1 micrometer to about 75 micrometers.

Figure 3:
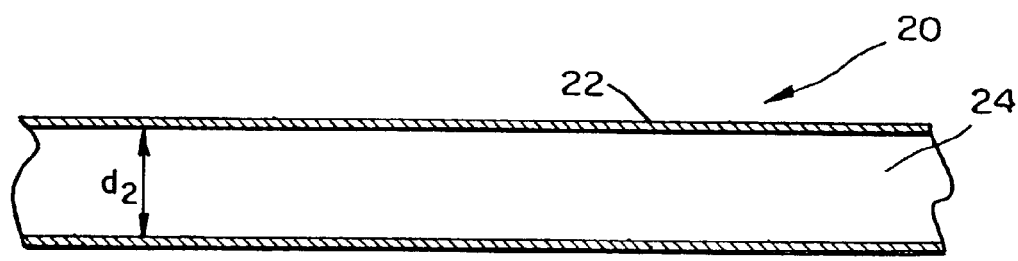
FIG. 3 is a side-elevational cross-sectional view of a thin-film catheter-sheath in accordance with the present invention.

FIG. 3 illustrates an embodiment of the inventive thin-film catheter-sheath 20 comprising a tubular catheter-sheath body 22 defining a central catheter-sheath lumen 24. Like the guidewire 10, the thin-film catheter-sheath 20 is fabricated by vacuum deposition of a biocompatible metal, preferably a nickel-titanium alloy, although conventional wrought process may be employed for certain embodiments such as those where compliance is required. The tubular catheter-sheath body 22 can be a monolayer of deposited material, or can comprise a plurality of laminated layers (not shown). A thin-film catheter-sheath according to the present invention preferably has an inner diameter $d_2$ between about 0.25 millimeters (mm) to about 6 millimeters (mm) to accommodate a wide range of self-expanding stents or other implantable and non-implantable medical devices such as filters, occlusion devices, valves, snare baskets, etc. Like the inventive guidewires, a thin-film catheter-sheath according to the present invention preferably has a wall thickness between about 0.1 micrometers to 75 micrometers.

Figure 4:
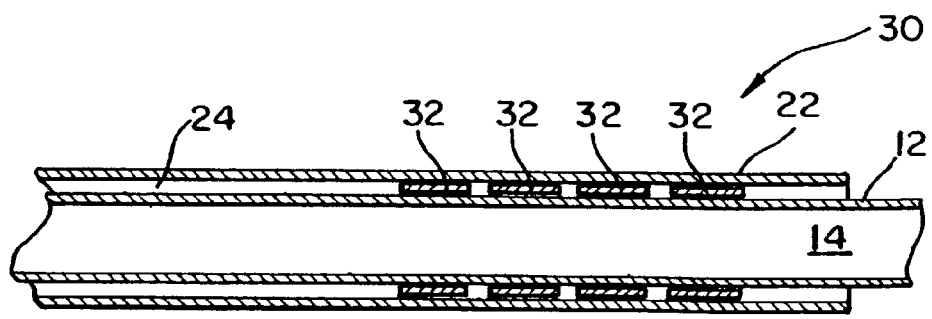
FIG. 4 is a side-elevational cross-sectional view of a thin-film catheter-sheath positioned concentrically about an inventive guidewire.

Referring now to FIG. 4, there is depicted a medical device delivery assembly 30 comprising a guidewire body 12 defining central guidewire lumen 14, a thin-film catheter-sheath body 22 defining central catheter-sheath lumen 24 concentrically positioned coaxially about the guidewire body 12 and a stent 32 which is concentrically positioned within central catheter-sheath lumen 24 and intermediate between the thin-film catheter-sheath body 22 and the guidewire body 12 and constrained therein by the thin-film catheter-sheath 20. The medical device used with the delivery assembly can be any medical device that can be delivered via a patient's vascular system, for example, a stent (as shown in FIG. 4), a graft, a stent-graft, a valve, a filter, an occluder, and a patch.

Figure 5A:
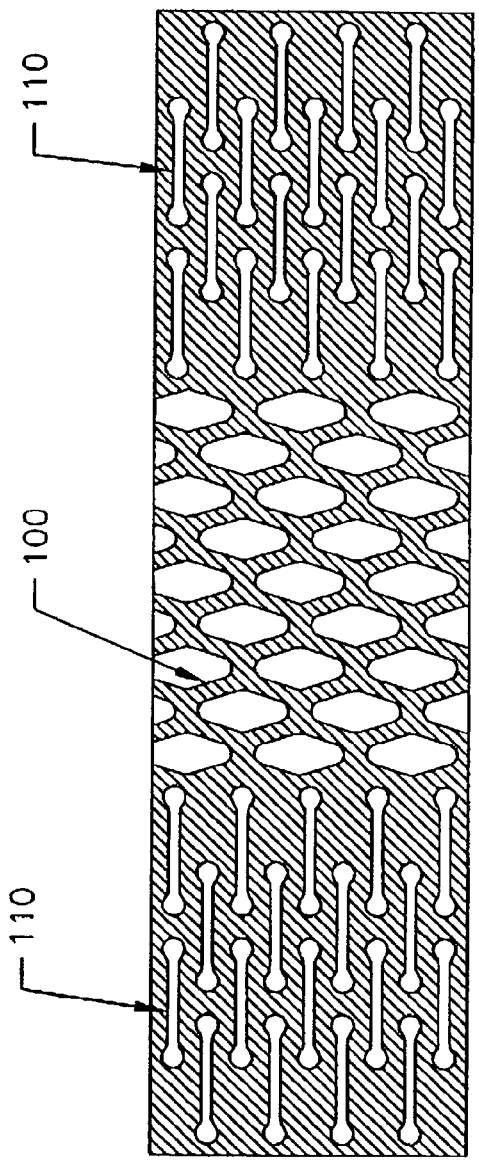
FIGS. 5A–5C illustrate a further embodiment of the thin-film catheter-sheath and/or guidewire incorporating microperforations of various patterns in accordance with the present invention.
Figure 5C:
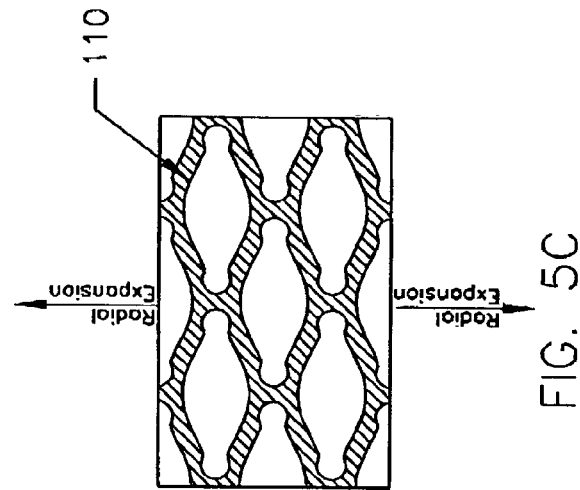
Figure 5B:
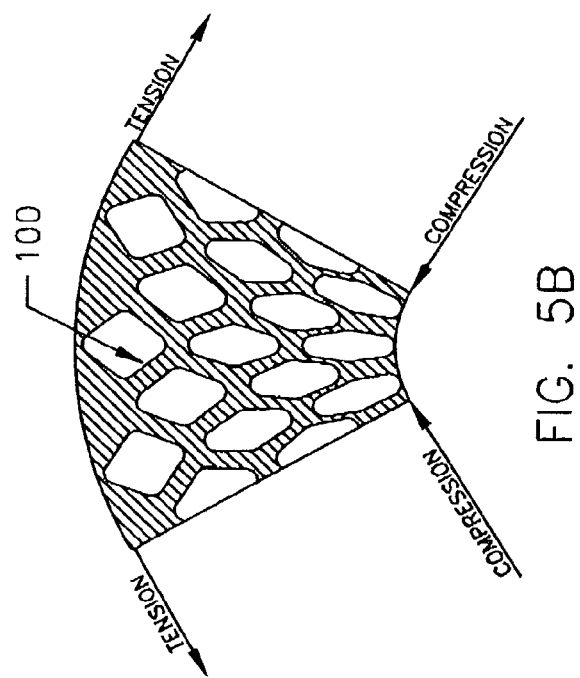

Turning now to FIGS. 5A–5C, a guidewire and/or catheter-sheath in accordance with a further embodiment of the invention is illustrated. As shown in FIG. 5A, an embodiment of the inventive guidewire or catheter-sheath is depicted in which areas of a guidewire or catheter-sheath body has microperforations. Microperforations, such as those referred to as 100 in FIGS. 5A and 5B impart longitudinal compliance, whereas microperforations such as those referred to as 110 in FIGS. 5A and 5C impart radial compliance. With particular reference to FIG. 5B, microperforations in the form of diamond shaped slots 100 around the circumference of the guidewire or catheter-sheath are provided to increase the longitudinal compliance of the guidewire or catheter-sheath in tension and compression thereby providing flexibility to negotiate tight radii. FIG. 5C shows how microperforations in the form of longitudinal slots 110 provide for radial compliance. In order to achieve desired compliance characteristics along the length of the catheter-sheath or guidewire, the microperforation (slot) patterns can be used in conjunction with one another in alternating patterns and/or leaving unpatterned sections along the length of the guidewire. Those skilled in the art will recognize that there are a number of different geometric patterns that can be used to form the microperforations, other than those described here, that will provide desired compliance characteristics to the inventive guidewire or catheter-sheath discussed herein. Skilled artisans will also recognize that microperforations can be created by any suitable technique such as etching a metal film, or during a vacuum deposition process by either masking a substrate during deposition, or etching a substrate to provide the pattern which will form the microperforations once the deposition has occurred.

In accordance with a preferred embodiment the present invention, the preferred vacuum deposition technique is selected from the group consisting of ion-beam assisted evaporative deposition and sputtering techniques. In ion beam-assisted evaporative deposition it is preferable to employ dual and simultaneous thermal electron beam evaporation with simultaneous ion bombardment of the material being deposited using an inert gas, such as argon, xenon, nitrogen or neon. Bombardment with inert gas ions during deposition serves to reduce void content by increasing the atomic packing density in the deposited material. The reduced void content in the deposited material allows the mechanical properties of that deposited material to be similar to the bulk material properties. Deposition rates up to 20 nanometers per second (nm/sec) are achievable using ion beam-assisted evaporative deposition techniques.

As used in this application, the articles "a" and "an" refer to one or more than one (i.e., to at least one) of the grammatical objects of the article. By way of example, "an element" means one element or more than one element.

EXAMPLE 1

In accordance with the preferred embodiment of fabricating the inventive microporous metallic implantable device in which the device is fabricated from vacuum deposited nitinol tube, a cylindrical deoxygenated copper substrate is provided. The substrate is mechanically and/or electropolished to provide a substantially uniform surface topography for accommodating metal deposition thereupon. A cylindrical hollow cathode magnetron sputtering deposition device was employed, in which the cathode was on the outside and the substrate was positioned along the longitudinal axis of the cathode. A cylindrical target consisting either of a nickel-titanium alloy having an atomic ratio of nickel to titanium of about 50—50% and which can be adjusted by spot welding nickel or titanium wires to the target, or a nickel cylinder having a plurality of titanium strips spot welded to the inner surface of the nickel cylinder, or a titanium cylinder having a plurality of nickel strips spot welded to the inner surface of the titanium cylinder is provided. It is known in the sputter deposition arts to cool a target within the deposition chamber by maintaining a thermal contact between the target and a cooling jacket within the cathode. In accordance with the present invention, it has been found useful to reduce the thermal cooling by thermally insulating the target from the cooling jacket within the cathode while still providing electrical contact to it. By insulating the target from the cooling jacket, the target is allowed to become hot within the reaction chamber. Two methods of thermally isolating the cylindrical target from the cooling jacket of the cathode were employed. First, a plurality of wires having a diameter of 0.0381 mm were spot welded around the outer circumference of the target to provide an equivalent spacing between the target and the cathode cooling jacket. Second, a tubular ceramic insulating sleeve was interposed between the outer circumference of the target and the cathode cooling jacket. Further, because the Ni—Ti sputtering yields can be dependant on target temperature, methods which allow the target to become uniformly hot are preferred.

The deposition chamber was evacuated to a pressure less than or about $2.5 \times 10^{-7}$ Torr and pre-cleaning of the substrate is conducted under vacuum. During the deposition, substrate temperature is preferably maintained within the range of 300 and 700 degrees Centigrade. It is preferable to apply a negative bias voltage between 0 and −1000 volts to the substrate, and preferably between −50 and −150 volts, which is sufficient to cause energetic species arriving at the surface of the substrate. During deposition, the gas pressure is maintained between 0.1 and 40 mTorr but preferably between 1 and 20 mTorr. Sputtering preferably occurs in the presence of an Argon atmosphere. The argon gas must be of high purity and special pumps may be employed to reduce oxygen partial pressure. Deposition times will vary depending upon the desired thickness of the deposited tubular film. After deposition, the plurality of microperforations are formed in the tube by removing regions of the deposited film by etching, such as chemical etching, ablation, such as by excimer laser or by electric discharge machining (EDM), or the like. After the plurality of microperforations are formed, the formed microporous film is removed from the copper substrate by exposing the substrate and film to a nitric acid bath for a period of time sufficient to remove or dissolve the copper substrate.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An assembly for delivering a medical device via a patient's vascular system, the assembly comprising: (a) a medical device; (b) a guidewire having a guidewire body, the guidewire body comprising a first thin-film of a first biocompatible metal formed by a vacuum deposition technique; and (c) a catheter-sheath having generally tubular catheter-sheath body, the catheter-sheath body comprising a second thin-film of a second biocompatible metal formed by a vacuum deposition technique, the catheter-sheath body defining a catheter-sheath lumen; wherein the guidewire is positioned coaxially within the lumen of the catheter-sheath, and wherein the medical device is concentrically positioned within a distal portion of the catheter-sheath lumen and intermediate the catheter-sheath body and the guidewire body, thereby forming the assembly, wherein at least one of the first thin-film and the second thin-film comprises a plurality of layers.

2. The assembly of claim 1, wherein the guidewire body is generally tubular.

3. The assembly of claim 1, wherein at least one of the guidewire body and the catheter-sheath body further comprises a plurality of microperforations that impart at least one of longitudinal compliance and radial compliance.

4. The assembly of claim 1, wherein the first and second biocompatible metals are similar.

5. The assembly of claim 1, wherein the medical device is selected from the group consisting of a stent, a graft, a stent-graft, a valve, a filter, an occluder, and a patch.

6. The assembly of claim 1, wherein a radiopaque metal is used to form at least on the layers.

7. The assembly of claim 1, wherein the first-thin film and the second thin-film each comprise a plurality of layers.

8. An assembly for delivering a medical device via a patient's vascular system, the assembly comprising: (a) a medical device; (b) a guidewire having a guidewire body, the guidewire body comprising a first thin-film of a first biocompatible metal formed by a vacuum deposition technique; and (c) a catheter-sheath having generally tubular catheter-sheath body, the catheter-sheath body comprising a second thin-film of a second biocompatible metal formed by a vacuum deposition technique, the catheter-sheath body defining a catheter-sheath lumen; wherein the guidewire is positioned coaxially within the lumen of the catheter-sheath, and wherein the medical device is concentrically positioned within a distal portion of the catheter-sheath lumen and intermediate the catheter-sheath body and the guidewire body, thereby forming the assembly, wherein the first thin-film and the second thin-film each comprise a plurality of layers.

9. The assembly of claim 8, wherein the guidewire body is generally tubular.

10. The assembly of claim 8, wherein at least one of the guidewire body and the catheter-sheath body further comprises a plurality of microperforations that impart at least one of longitudinal compliance and radial compliance.

11. The assembly of claim 8, wherein the first and second biocompatible metals are similar.

12. The assembly of claim 8, wherein the medical device is selected from the group consisting of a stein, a graft, a stent-graft, a valve, a filter, an occiuder, and a patch.

13. The assembly of claim 8, wherein a radiopaque metal is used to form at least on the layers.

* * * * *

UNITED STATES PATENT AND TRADEMARK OFFICE
CERTIFICATE OF CORRECTION

| | | |
|---|---|---|
| PATENT NO. | : 7,235,092 B2 | Page 1 of 1 |
| APPLICATION NO. | : 10/136001 | |
| DATED | : June 26, 2007 | |
| INVENTOR(S) | : Christopher E. Banas et al. | |

It is certified that error appears in the above-identified patent and that said Letters Patent is hereby corrected as shown below:

On the title page item (56), Col. 2, line 32,
Page 2: U.S. Patent Documents

Add -- 6,428,569  A  8/2002  Brown --

Item (56), under other publications
Page 3 - Column 1 - Line 46:

Delete " and. "

Item (56), under other publications
Page 3 - Column 2 - Line 53:

Delete " nickel-tetanium " and insert -- nickel-titanium --

Column 12 - Line 29:

Delete " 2.5 " and insert -- 2-5 --

Signed and Sealed this

Twenty-seventh Day of November, 2007

JON W. DUDAS
*Director of the United States Patent and Trademark Office*